US00PP16303P2

(12) United States Plant Patent
Olesen

(10) Patent No.: US PP16,303 P2
(45) Date of Patent: Feb. 28, 2006

(54) SHRUB ROSE PLANT NAMED 'POULCOT001'

(50) Latin Name: ***Rosa* hybrid**
Varietal Denomination: Poulcot001

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 101 days.

(21) Appl. No.: 11/001,914

(22) Filed: Dec. 1, 2004

(51) Int. Cl.
*A01H 5/00* (2006.01)

(52) U.S. Cl. ..... Plt./104
(58) Field of Classification Search ..... Plt./104, Plt./145, 134
See application file for complete search history.

*Primary Examiner*—Anne Marie Grunberg
*Assistant Examiner*—June Hwu

(57) ABSTRACT

A new garden rose plant of the shrub rose class which has abundant, yellow flowers and attractive foliage. This new and distinct variety has shown to be uniform and stable in the resulting generations from asexual propagation.

1 Drawing Sheet

Botanical classification: *Rosa* hybrid.
Variety denomination: 'Poulcot001'.

SUMMARY OF THE INVENTION

The present invention constitutes a new and distinct variety of garden rose plant that originated from a controlled crossing between the female seed parent, a rose by the same inventors named 'Pouldiram' described and illustrated in U.S. Pat. No. 12,568, and issued on Apr. 23, 2002, and the male pollen parent plant, an unnamed seedling.

The two parents were crossed during the summer of 1994, and the resulting seeds were planted in a controlled environment in Fredensborg, Denmark. The new variety is named 'Poulcot001'.

The new variety may be distinguished from its female seed parent, 'Pouldiram', by the following combination of characteristics:

1. 'Pouldiram' has white flowers. Flowers 'Poulcot001' are yellow.
2. 'Pouldiram' has a petal count of 12 to 18. 'Poulcot001' is 20 to 25.

'Poulcot003' may be distinguished from the male pollen parent by the following combination of characteristics:

1. The pollen parent has larger flowers than 'Poulcot001'.
2. Stems of the male pollen parent have fewer thorns than 'Poulcot001'.

The objective of the hybridization of this rose variety was to create a new and distinct variety for garden use with unique qualities, such as:

1. Uniform and abundant yellow flowers;
2. Vigorous, but compact growth;
3. Propagates easily from soft wood cuttings;
4. Exhibits a profusion of rose hips;
3. Exceptional disease resistance.

This combination of qualities is not present in previously available commercial cultivars of this type, known to the inventors, and distinguish 'Poulcot001' from all other varieties of which we are aware.

As part of the rose development program, Mogens N. Olesen germinated the seeds from the aforementioned hybridization during winter of 1994 and conducted evaluations on the resulting seedlings in a controlled environment in Fredensborg, Denmark.

'Poulcot001' was selected in the spring of 1995 by the inventor as a single plant from the progeny of the aforementioned hybridization.

Asexual reproduction of 'Poulcot001' by traditional budding and rooted cuttings was first done by Mogens N. Olesen in the nursery in Fredensborg, Denmark in July 1995. This initial and other subsequent asexual propagations conducted in controlled environments have demonstrated that the characteristics of 'Poulcot001' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcot001'. Specifically illustrated in the drawing:

FIG. 1.1; Open flowers, viewed from above, and attached to stem;

FIG. 1.2; Petals detached;

FIG. 1.3; Flower bud closed and partially open;

FIG. 1.4; Sepals, receptacle, and peduncle;

FIG. 1.5; Juvenile leaves and stem;

FIG. 1.6; Mature leaf;

FIG. 1.7; Bare stems, exhibiting thorns.

DETAILED DESCRIPTION OF THE VARIETY

The following is a description of 'Poulcot001', as observed in its growth in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulaksel', a rose variety from the same inventors described and illustrated in U.S. Plant patent application Ser. No. 10/647,013 filed Aug. 21, 2003, are compared to 'Poulcot001' in Chart 1.

CHART 1

| | 'Poulcot001' | 'Poulaksel' |
|---|---|---|
| General tonality. | Yellow Group 5C. | Yellow Group 4B. |
| Petal count. | 20 to 25. | 18 to 20. |
| Growth dimensions | 40 cm tall by 100 cm wide | 100 cm tall by 100 cm wide |

FLOWER AND FLOWER BUD

Blooming habit: Continuous.

Flower bud:

*Size.*—Upon opening, 20 mm in length from base of receptacle to end of bud. Bud diameter is normally 8 to 10 mm.

*Bud form.*—Ovate.

*Bud color.*—As sepals unfold, petals are Yellow Group 8B.

*Sepal inner surface.*—Color: Yellow-Green Group 147C. At the apex of sepals margins exhibit anthocyanic pigments the color of Greyed-Red 179A. Surface: Strongly pubescent.

*Sepal outer surface.*—Color: Yellow-Green Group 144A. Anthocyanic pigments observed on the margins of the sepal apex the color of Greyed-Red 179A. Texture: Smooth with few stipitate glands.

*Sepal shape.*—Apex: Cirrhose. Base: Flat at union with receptacle.

*Sepal margin.*—Margins have medium foliaceous appendages on three of the five sepals. Stipitate glands are sparsely present.

*Sepal size.*—23 mm (l)×6 mm (w).

*Receptacle.*—Texture: Smooth. Shape: Urn shaped. Size: 8 mm (h)×5 mm (w). Color: Yellow-Green Group 144A.

*Peduncle.*—Surface: Smooth. Length: 10 to 30 mm. Length varies according to placement of rose stem. Diameter: 4 mm on average. Color: Yellow-Green Group 138B.

*Pedicel.*—Surface: Slightly rough with stipitate glands. Length: 20 mm on average. Diameter: 2 mm on average. Color: Yellow-Green Group 144A. Anthocyanic pigments Greyed-Red Group 180A. Strength: Medium. Scent: Stipitate glands exude a strong spicy scent when touched.

Flower bud development: Flower buds are borne in clusters of 7 flower buds per stem. Inflorescence type is a raceme.

Flower bloom:

*Fragrance.*—Little or no scent.

*Duration.*—The blooms have a duration on the plant of 6 to 10 days. Petals fall cleanly away from plant after flowers have fully matured.

*Size.*—Flower diameter is 42 mm when fully open. Depth is 16 mm.

*Flower shape.*—Semi-double. When fully open, flowers are nearly flat.

*Shape of flower, side view.*—Upon opening, Upper portion: Flat. Lower portion: Flat. After opening, Upper portion: Flat. Lower portion: Slightly concave.

*Petalage.*—Under normal conditions, flowers have 20 to 25 petals total, 5 of which are petaloids.

*Petal color.*—Upon opening, outer petals: Upper surface: Yellow Group 4C to 5C. Lower surface: Yellow Group 4C. Upon opening, inner petals: Upper surface: Yellow Group 4C to 5C. Lower surface: Yellow Group 4C. Basal petal spots, upon opening: Upper surface: Yellow Group 5B. Lower surface: Yellow Group 5B. After opening, outer petals Upper surface: Yellow Group 4C to 5C. Lower surface: Yellow Group 4C. Upon opening, inner petals: Upper surface: Yellow Group 4C to 5C. Lower surface: Yellow Group 4C. Basal petal spots, upon opening: Upper surface: Yellow Group 5B. Lower surface: Yellow Group 5B.

General tonality: On open flower Yellow Group 5C. No change in the general tonality at the end of the $5^{th}$ day. Afterwards, general tonality is Yellow Group 4C.

Petals:

*Petal reflex.*—Flat.

*Margin.*—Entire, point at the center observed.

*Shape.*—Narrow elliptic. Apex: Cuspidate. Base: Acute.

*Average size.*—22 mm (l)×19 mm (w).

*Texture.*—Smooth.

*Thickness.*—Thin.

*Arrangement.*—Not Formal.

Petaloids:

*Quantity.*—5 on average.

*Shape.*—Generally elliptic and irregular.

*Color.*—Yellow Group 4C to 5C.

*Size.*—10 to 15 mm (l)×6 mm (w).

Reproductive organs:

*Pollen.*—None observed.

*Anthers.*—Size: 2.5 mm in length. Color: Yellow-Orange Group 15A. Quantity: 90 on average.

*Filaments.*—Color: Yellow Group 7A. Length: 6 mm.

*Pistils.*—Length: 5 mm. Quantity: 27 on average.

*Stigmas.*—Level in location relative to the length of the filaments and the height of the anthers. Color: Yellow-Green Group 145C.

*Styles.*—Color: Yellow-Green Group 145B.

PLANT

Plant growth: Spreading and low growing. When grown as a budded field grown plant on *Rosa multiflora* understock, the average height of the plant is 40 cm and the average width is 40 to 60 cm.

Stems:

*Color.*—Juvenile growth: Yellow-Green Group 144C to 144B. Mature growth: Green Group 138B.

*Length.*—35 to 45 cm from the base of the plant to the flowering portion.

*Diameter.*—8 mm.

*Internodes.*—One mature canes, there is an average distance of 21 mm between nodes.

*Surface texture.*—Young wood: Smooth. Older wood: Smooth.

Thorns:

*Incidence.*—14 thorns per 10 cm of stem on average.

*Size.*—9 mm.

*Shape.*—Upper side: Concave. Lower side: Deeply concave.

*Color.*—Juvenile and mature thorns are Yellow-Green Group N144A.

Plant foliage: Normally 7 leaflets in middle of the stem.

*Compound leaf.*—70 mm (l)×32 (w).

*Quantity.*—4 to 5 leaves per 10 cm of stem on average.

*Color of mature foliage.*—Upper side: Green Group 137A to Yellow-Green Group 147A. Lower side: Yellow-Green Group 147B.

*Color of juvenile foliage.*—Upper side: Yellow-Green Group N144A. Margins are Greyed-Orange Group 173A. Lower side: Yellow-Green Group 144B.

Plant leaves and leaflets:

*Stipules.*—Size: 18 mm in length. Shape: Linear, slightly broad based with outward extending apecies. Margins: Entire with stipitate glands. Color: Yellow-Green Group 146A.

*Petiole.*—Length: 22 mm. Diameter: 2 mm.

*Upper surface.*—Color: Yellow-Green Group 146A. Observations: Few stipitate glands.

*Lower surface.*—Color: Yellow-Green Group 146C. Texture: Smooth.

*Rachis.*—Length: 32 mm. Upper surface: Color: Yellow-Green Group 146A.

*Lower surface.*—Color: Yellow-Green Group 146C. Observations: Few stipitate glands. Small prickles observed.

*Leaflet.*—Edge: Serrated. Size: Average size of the terminal leaflet on normal leaves is 21 mm (l)×12 mm (w). Shape: Elliptical. Base: Obtuse. Apex: Cuspidate. Texture: Smooth. Thickness: Average. Arrangement: Odd pinnate. Venation: Reticulate. Glossiness: Somewhat glossy.

Disease resistance: Above average resistance to mildew, rust, black spot, and Botrytis under normal growing conditions in Jackson County, Oreg.

Cold hardiness: The variety 'Poulcot001' has been found to be cold tolerant to USDA Cold Hardiness Zone 6.

It is claimed:

1. A new and distinct variety of rose plant of the shrub rose class named 'Poulcot001', illustrated and described herein as a distinct and novel rose variety due to its abundant yellow flowers, plentiful rose hips, exceptional disease resistance, and extended period of bloom.

* * * * *

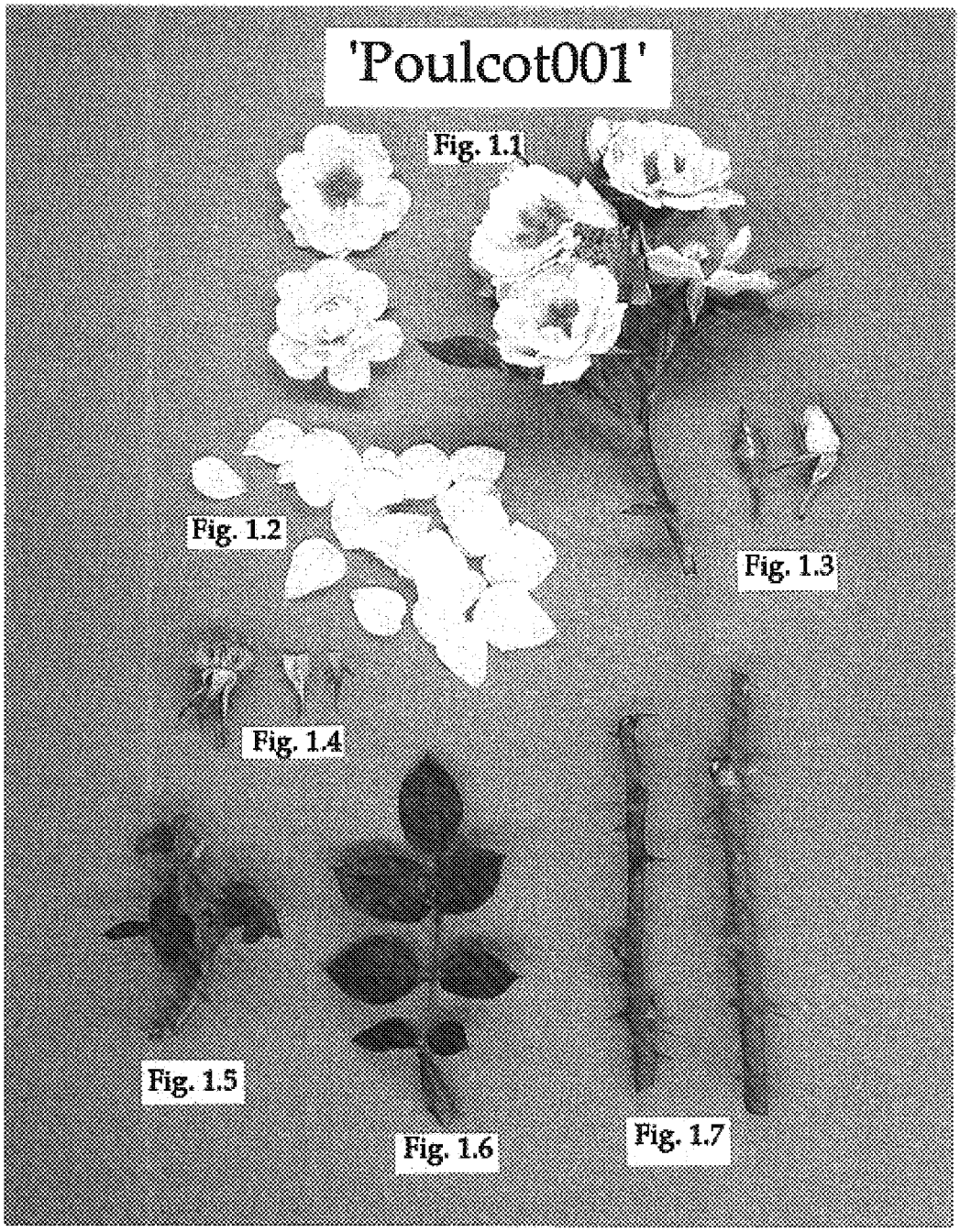
'Poulcot001'
Fig. 1.1
Fig. 1.2
Fig. 1.3
Fig. 1.4
Fig. 1.5
Fig. 1.6
Fig. 1.7